US005639627A

United States Patent [19]

Tanaka

[11] Patent Number: 5,639,627
[45] Date of Patent: Jun. 17, 1997

[54] METHOD FOR ASSAYING SPECIFIC ANTIBODY

[75] Inventor: Satoshi Tanaka, Ibaraki, Japan

[73] Assignee: Sumitomo Pharmaceuticals Co., Ltd., Osaka, Japan

[21] Appl. No.: 495,618

[22] PCT Filed: Feb. 4, 1993

[86] PCT No.: PCT/JP93/00143

§ 371 Date: Aug. 3, 1995

§ 102(e) Date: Aug. 3, 1995

[87] PCT Pub. No.: WO94/18566

PCT Pub. Date: Aug. 18, 1994

[51] Int. Cl.⁶ .................. G01N 33/53; G01N 33/543; G01N 33/536
[52] U.S. Cl. .................. 435/7.95; 435/7.9; 435/7.94; 436/518; 436/536
[58] Field of Search .................. 436/518, 536; 435/7.9, 7.94, 7.95

[56] References Cited

U.S. PATENT DOCUMENTS 4,945,042  7/1990  Geiger et al. .

FOREIGN PATENT DOCUMENTS

| 256011 | 8/1985 | German Dem. Rep. . |
| 60-196669 | 5/1985 | Japan . |
| 2247565 | 3/1990 | Japan . |
| 3082962 | 8/1991 | Japan . |

OTHER PUBLICATIONS

Analytical Letters, vol. 21, (11), pp. 2033–2048, Takeyuki Kohno et al, "Novel and Sensitive Enzyme Immunoassay for Anti–Thyroglobulin Antibodies in Serum Using . . . Conjugate".
Kohno et al., 1988, Analytical Letters, 21: 2033–2048.
Derwent Abstract (Accession Number: 90–198361; Ishikawa et al).

*Primary Examiner*—James C. Housel
*Assistant Examiner*—Jennifer Shaver
*Attorney, Agent, or Firm*—Sughrue, Mion, Zinn, Macpeak & Seas

[57] ABSTRACT

A method for assaying a specific antibody, comprising the following steps (A), (B) and (C):

(A): forming a complex of a labeled antigen-a specific antibody-a carrier-bound antigen in a first reaction system comprising a mixture of the antigen (labeled antigen) against the specific antibody to be assayed, the antigen being bound to the label in advance, the antigen (carrier-bound antigen) against the above-mentioned specific antibody, the antigen being bound to the carrier in advance, and a liquid sample comprising the above-mentioned specific antibody, (B): mixing the above-mentioned separated carrier and a labeled antigen same as above after separating the above-mentioned carrier after reaction from the above-mentioned first reaction system to give a second reaction system, and (C): assaying, after separating the above-mentioned carrier after reaction from the above-mentioned second reaction system, the amount of the label bound to the above-mentioned separated carrier. According to the present invention, a complete complex of carrier-bound antigen-specific antibody-labeled antigen is formed in the first reaction system wherein the two antigens and the specific antibody are reacted by mixing the carrier-bound antigen, the labeled antigen and the liquid sample comprising the specific antibody to be assayed. When an incomplete complex of carrier-bound antigen-specific antibody is present in the second reaction system, a complete complex can be formed by mixing the separated carrier and the labeled antigen after separating the carrier after reaction from the first reaction system. Accordingly, the prozoning phenomenon can be eliminated and the target specific antibody can be assayed with high sensitivity by assaying the amount of the label bound to the carrier, after separating the carrier after reaction from the second reaction system.

10 Claims, 2 Drawing Sheets

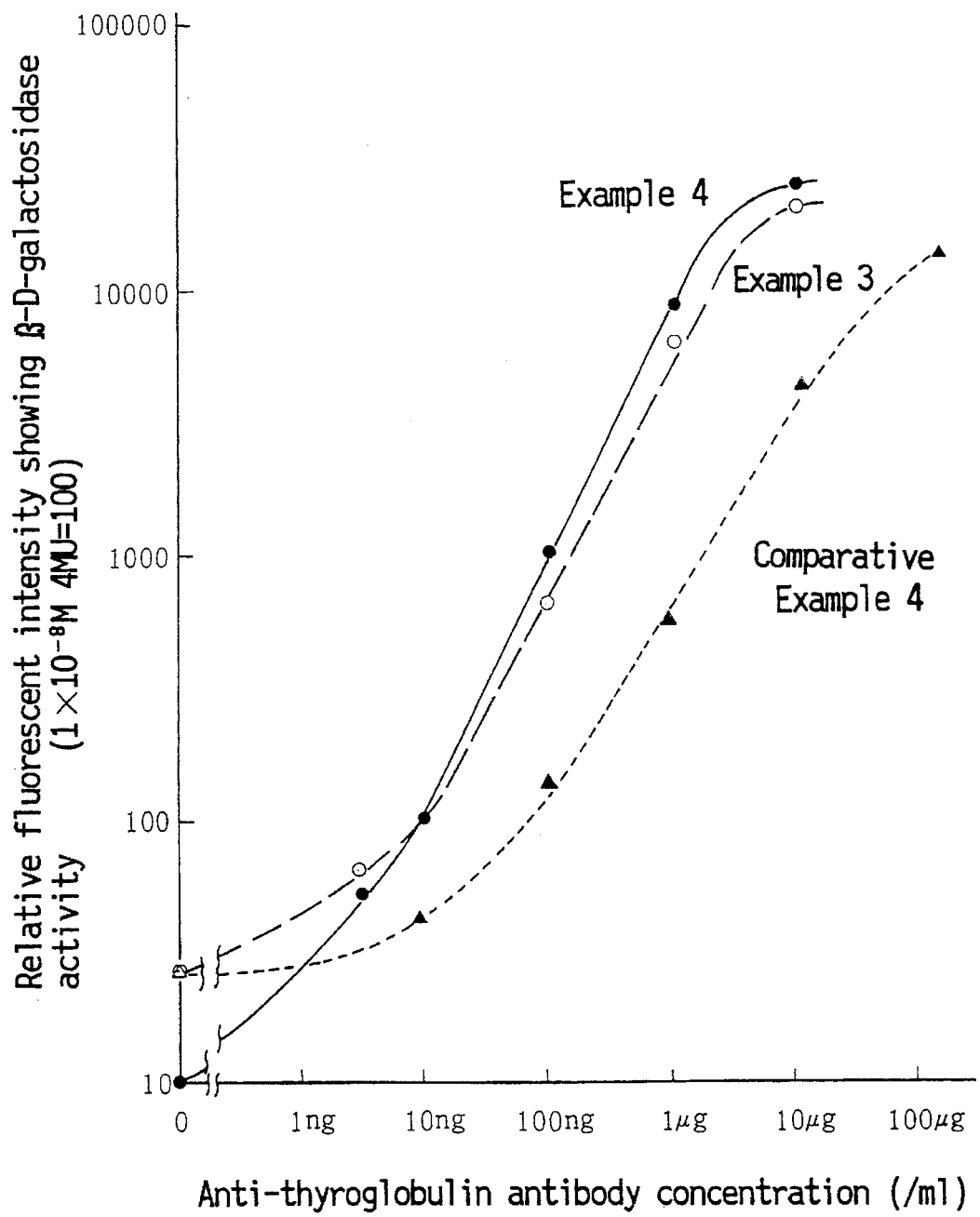

5,639,627

METHOD FOR ASSAYING SPECIFIC ANTIBODY

TECHNICAL FIELD

The present invention relates to a method for high sensitivity assay of an antibody specific to a certain antigen.

BACKGROUND ART

There have been reported various methods for quantitative assay of antibody, which are based on the principles of immunoassay. Typical techniques include, for example, agglutination, competitive assay and sandwich method. From the aspect of sensitivity, it is well known that assays based on the principles of the sandwich method can achieve their highest.

The sandwich method for specific antibody includes, for example, a method comprising bringing a carrier bound with an antigen into contact with a liquid sample containing the antibody to be assayed, reacting the carrier with a labeled anti-Ig antibody (secondary antibody) and assaying the antibody level from the amount of the label bound to the carrier. This method is defective in that the non-specific antibodies contained in the liquid sample in a large amount are also adsorbed to the carrier to increase the background, thus making higher detection sensitivity difficult to achieve.

Another method includes binding an anti-Ig antibody to a carrier, bringing the carrier into contact with a liquid sample and allowing a (labeled) antigen specific to the antibody to be assayed, to react with the antibody. In this method, the defect lies in the fact that binding the object antibody to the carrier is prevented by non-specific antibodies contained in greater amounts in the liquid sample and signals cannot be obtained in sufficient amounts. Consequently, high sensitive assay is difficult like the above-mentioned method.

Another method includes bringing a carrier bound with an antigen into contact with a liquid sample to allow reaction of a labeled antigen. This method is defective in that signals cannot be obtained in sufficient amounts in a short time due to the low reactivity of the labeled antigen to the antibody bound to the carrier. Again, high sensitivity assay by this method is associated with difficulty.

As a method for highly sensitive and easy assay of an antibody, a method has been recently reported which includes reacting a labeled antigen and an antigen bound to hapten with the object antibody in a liquid sample in a liquid phase, trapping the resultant complex on a carrier using an anti-hapten antibody, and assaying the complex [Ishikawa et al., Analytical Letters, vol. 21, p. 2033 (1988), DE 3705686 to Thomas Geiger et al.]. This method is expected to achieve high sensitive assay. However, the method is defective in that the assay components are complicated and it rather gives lower assay values (prozoning phenomenon) when the antibody to be assayed is present in considerably great amounts in the liquid sample.

DISCLOSURE OF THE INVENTION

An object of the present invention is to develop a method for assaying a specific antibody, which can be performed as easily as the conventional sandwich method, has high sensitivity and is free of the prozoning phenomenon.

The present inventors have found that the object specific antibody can be assayed with high sensitivity and the prozoning phenomenon can be eliminated by, in a reaction system wherein a carrier-bound antigen, a labeled antigen, and a liquid sample containing the specific antibody to be assayed are simultaneously mixed to react the above-mentioned two antigens with the above-mentioned specific antibody, forming a complex of the carrier-bound antigen-specific antibody-labeled antigen, separating said carrier after the reaction from the aforementioned reaction system, and again mixing the aforementioned separated carrier and the aforementioned labeled antigen, which resulted in the completion of the present invention.

That is, the present invention provides a method for assaying a specific antibody, comprising the following steps (A), (B) and (C):

(A): forming a complex of a labeled antigen-a specific antibody-a carrier-bound antigen in a first reaction system comprising a mixture of the antigen (labeled antigen) against the specific antibody to be assayed, the antigen being bound to the label in advance, the antigen (carrier-bound antigen) against the above-mentioned specific antibody, the antigen being bound to the carrier in advance, and a liquid sample comprising the above-mentioned specific antibody, (B): mixing the above-mentioned separated carrier and a labeled antigen same as above after separating the above-mentioned carrier after reaction from the above-mentioned first reaction system to give a second reaction system, and (C): assaying, after separating the above-mentioned carrier after reaction from the above-mentioned second reaction system, the amount of the label bound to the above-mentioned separated carrier.

BRIEF DESCRIPTION OF THE DRAWINGS

FIG. 2 shows calibration curves of anti-thyroglobulin antibodies in Examples 3 and 4 and Comparative Example 4, wherein the abscissa shows the concentration of the anti-thyroglobulin antibody in the sample and the ordinate shows the amount of the signal derived from the activity of the $\beta$-D-galactosidase bound to respective solid phases.

DETAILED DESCRIPTION OF THE INVENTION

Figure 1:
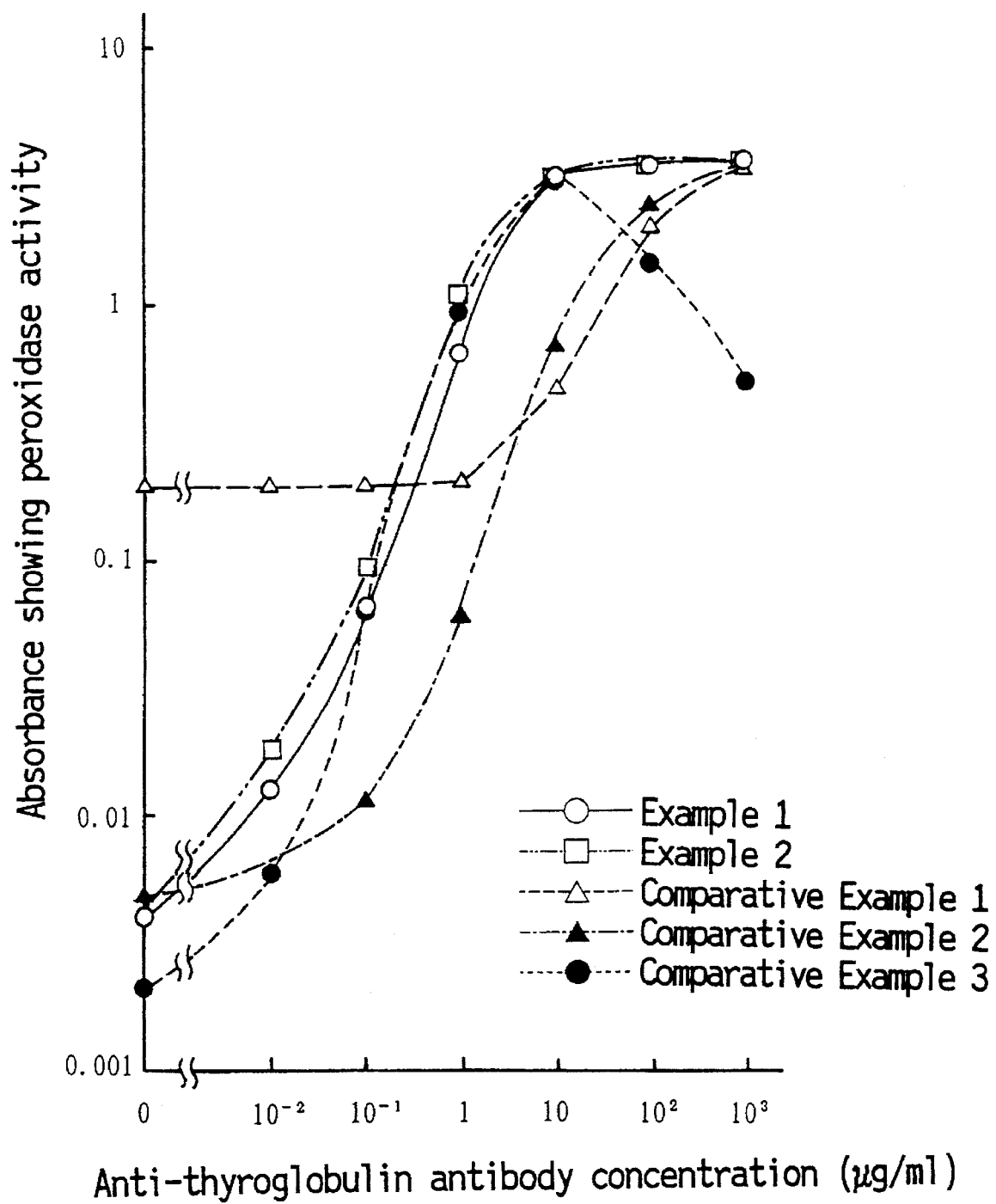
FIG. 1 shows calibration curves of anti-thyroglobulin antibodies in Examples 1 and 2 and Comparative Examples 1 to 3, wherein the abscissa shows the concentration of the anti-thyroglobulin antibody in the sample and the ordinate shows the amount of the signal derived from the activity of the peroxidase bound to respective solid phases.

The present invention is explained by the order of the steps.

(A)

(A) is a step for improving sensitivity by an easy and simple method. In (A), the amount of the labeled antigen to be added to the first reaction system is desirably set for such an amount that makes the rate of the reaction between the labeled antigen and the specific antibody in a liquid phase in the liquid sample, and the rate of the reaction between the carrier-bound antigen and the specific antibody almost the same. In the case of conventional immunoassay, the molecular molar ratio of the carrier-bound antigen to the labeled antigen is 1:1–50:1, preferably 5:1–20:1.

In the present invention, by an antigen is meant a specific antigen, an anti-idiotype antibody or a component such as hapten bound to a suitable carrier, which is capable of developing an antigen-antibody reaction with the specific antibody to be assayed.

As the liquid sample, exemplified are body fluids such as serum, plasma, cerebrospinal fluid, saliva and urine, and buffers.

The specific antibody to be assayed in the present invention is every antibody which can be substantially assayed by conventional immunoassay if an antigen which is specifically recognized by the antibody is used, and according to the present invention, assay of such specific antibody is attainable. For example, assays of autoantibodies such as assay of anti-DNA antibody using a nucleic acid, assay of rheumatoid factor using an immunoaggregate, assay of anti-mitochondria antibody using pyruvate dehydrogenase, assay of anti-microsomal antibody using thyroid peroxidase, assay of anti-thyroglobulin antibody using thyroglobulin, assay of anti-TSH receptor antibody using TSH receptor, assay of anti-insulin antibody using insulin and assay of anti-acetylcholine receptor antibody using acetylcholine receptor; assay of antiviral antibodies such as anti-HBV antibody and anti-HIV antibody, using virus antigen; assay of antibodies against microorganisms; assay of antibodies against protein preparations such as interferon and human growth hormone; and assay of antibodies against allergens in allergic diseases are included.

The label used for the labeled antigen which is labeled in advance may be any substance usable for the assay in immunological assay, and is exemplified by enzyme, radioactive substance, luminescent substance, fluorescent substance and metal compound. For example, enzyme is exemplified by peroxidase, β-D-galactosidase and alkaline phosphatase; radioactive substance is exemplified by iodine and hydrogen; fluorescent substance is exemplified by fluorescein isothiocyanate; luminescent substance is exemplified by acridinium salt; and metal compound is exemplified by europium ($Eu^{3+}$).

The aforementioned labels can be bound to antigens by any binding method reported to be usable for binding a label to an antibody or antigen in conventional immunological assay. When the label is an enzyme, covalent linking via a suitable multifunctional crosslinking agent is preferable. The crosslinking reaction is advantageously carried out by utilizing the reaction of, for example, amino group and aldehyde group (Schiff reaction), amino group and active ester, thiol group and maleimide group, and thiol group and pyridyl•disulfide group, since antigen and enzyme do not lose their activity. These reactions are all carried out by incubation in a buffer having a pH of 6–9 at 4–37° C. for several minutes to several days. When the label is a radioactive substance, $^{125}I$ can be introduced into, for example, an antigen having a tyrosine residue in molecule, by reacting the antigen with [$^{125}I$] sodium iodide in the presence of an oxidizing agent such as chloramine T at 0–10° C. for several to several dozen minutes.

These labels may be bound to antigens via a suitable spacer which does not affect the antigen-antibody reactions in (A), (B) and (C). When the antigen has a low molecular weight, the use of such spacer is particularly preferable. Examples of the spacer include non-specific rabbit IgG, bovine serum albumin, dextran and hydrocarbon (carbon number 4–10) having a suitable length.

There is no particular limitation imposed on the carrier as long as it does not impair the object of the invention, and those used in conventional immunological assay suffice for use. For example, polystyrene, polyacryl, Teflon, paper, glass and agarose can be used. The shape thereof is not particularly limited.

An antigen can be bonded to a carrier by a known method for forming a carrier in immunological assay. In general terms, physical adsorption utilizing a hydrophobic interaction between carrier and antigen is applied when an antigen is a protein having a relatively large molecular weight. Generally, a carrier is immersed in a buffer (in the range of from pH 7 to pH 9.5) containing an antigen at a concentration of several dozen—several hundred mg/l, at 4–37° C. for several hours to several days. When the antigen has a low degree of hydrophobic interaction with a carrier, a functional group such as amino and carboxyl is introduced in advance into the carrier and the antigen is covalently linked via a crosslinking agent such as glutaraldehyde, or the antigen is mixed with a suitable monomer and immobilized by polymerization using γ ray and the like. When the antigen has a low molecular weight, it is bonded to a carrier via a spacer which does not affect the steps of (A) to (C). Examples of the spacer include non-specific rabbit IgG, bovine serum albumin, dextran, hapten and antibody, and biotin and avidin.

In (A), the first reaction system is obtained by mixing a specific antibody in a liquid sample, a labeled antigen and a carrier-bound antigen, after which a complex of the labeled antigen-specific antibody-carrier-bound antigen is formed in this first reaction system under the conditions generally used for conventional antigen-antibody reaction. In general, a complex is formed at 0–45° C. for several hours-several dozens of hours, preferably at 20–37° C. for 1–6 hours of reaction.

(B)

(B) is a step for eliminating the prozoning phenomenon. When the amount of the specific antibody to be assayed in a liquid sample is present in excess in comparison with the amount of the antibody that an antigen bound to a carrier can trap, the steps of (A) and (C) alone results in an excess amount of specific antibody binding not to the carrier-bound antigen but to labeled antigen to form an incomplete complex of labeled antigen-specific antibody. The excess specific antibody consumes labeled antigen necessary for forming a complete complex, causing insufficient level of the labeled antigen in comparison with the amount of specific antibody bound to the carrier-bound antigen, which can sometimes result in partial formation of an incomplete complex of specific antibody-carrier-bound antigen. Consequently, the assay values showing the amount of the antibody bound to the carrier-bound antigen becomes lower than those corresponding to the amount of the antibody actually bound (prozoning phenomenon). The instant step supplements the labeled antigen consumed by the excess antibody in the liquid sample and allows the labeled antigen to be bound to the incomplete complex of the specific antibody-carrier-bound antigen to form a complete complex of labeled antigen-specific antibody-carrier-bound antigen, which enables compensation of the lowered signal values caused by the prozoning phenomenon.

The method for separating the aforementioned carrier after reaction from the aforementioned first reaction system, namely, a method for separating, in the first reaction system after (A), an incomplete complex of labeled antigen-specific antibody, unreacted specific antibody and unreacted labeled antigen, from a complete complex of labeled antigen-specific antibody-carrier-bound antigen, an incomplete complex of specific antibody-carrier-bound antigen and unreacted carrier-bound antigen, can be any method which is employed in conventional immunological assay using carrier.

Then, the carrier separated from the above-mentioned first reaction system is again mixed with a labeled antigen to give a second reaction system. When the carrier separated from the first reaction system comprises an incomplete complex of specific antibody-carrier-bound antigen, the carrier separated from the first reaction system is preferably washed before mixing with the labeled antigen to ensure binding of the labeled antigen to the incomplete complex. The carrier is washed under the conditions conventionally used in sandwich method. In general, a solution containing a mild surfactant such as Tween 20 is brought into contact with the carrier separated from the first reaction system for a certain time and the solution and the carrier are separated. This step is repeated several times.

While the amount of the labeled antigen to be mixed in (B) is not subject to any particular limitation, mixing of the antigen in excess increases non-specific binding of the labeled antigen to the carrier after separation, which in turn increases background and lowers sensitivity. Accordingly, the antigen is desirably used in an amount necessary and sufficient to complete the reaction. Generally, the amount is from 1/10 to the same amount as the labeled antigen used in (A).

The reaction between the labeled antigen and the incomplete complex bound to the carrier (carrier-bound antigen-specific antibody) in the second reaction system is carried out under the conditions used for conventional antigen-antibody reaction. The reaction generally proceeds at 0–45° C. for several dozen minutes to several hours, preferably 20–37° C. for 30 minutes to 2 hours to give a complete complex (labeled antigen-specific antibody-carrier-bound antigen).

(C)

In (C), the method for separating the carrier after reaction from the aforementioned second reaction system and the method for washing the carrier after separation may be any method employed in conventional immunological assay using carrier. Washing is preferably performed by adding a washing solution to the reaction system, leaving the mixture for several minutes and removing the washing solution. The amount of the label bound to the carrier is determined by detection of radiation, detection of fluorescence, detection of absorbance, spectrometry, atomic absorption analysis and the like, depending on the peculiar nature of the label introduced into the antigen in (A).

For determination of radiation, a γ counter or liquid scintillation counter is used for several dozen seconds to several minutes. When an enzyme is used as a label, a substrate capable of emitting a detectable signal in response to the action of the enzyme is added and the signal is detected by the detection step as mentioned above. For example, when the enzyme is horseradish peroxidase, the substrate can be, for example, $H_2O_2$ and o-phenylenediamine (detection of absorbance) or $H_2O_2$ and o-hydroxyphenylpropionic acid (fluorescence detection). When the enzyme is, for example, β-D-galactosidase, the substrate can be, for example, ρ-nitrophenyl-β-D-galactopyranoside (detection of absorbance) or 4-methylumbelliferyl-β-D-galactose (fluorescence detection). For example, when the enzyme is alkaline phosphatase, the substrate can be, for example, ρ-nitrophenylphosphate (detection of absorbance) or 4-methylumbelliferylphosphate (fluorescence detection). These reactions are carried out at 20–37° C. for several minutes to several hours.

The present invention is described in more detail by referring to Examples, to which the invention is not limited.

EXAMPLE 1

Purification of thyroglobulin

Human thyroglobulin (10 mg, UCB Bioproducts, Belgium) was purified by a method using DE-52 cellulose (Whatman, Kent, UK) column [Otaki et al., Journal of Clinical Endocrinology and Metabolite, vol. 52, p. 239 (1981)].

The above-mentioned purified thyroglobulin (7.0 mg) was eluted with 0.1M sodium phosphate buffer, pH 7.0, using rabbit (anti-human-IgG γ-chain) IgG immobilized on Sepharose 4B column (1.0×4.5 cm), and subjected to gel filtration using the same buffer and Ultrogel AcA22 (1.6×45 cm, LKB, Stockholm, Sweden). The purity of the purified product was confirmed by SDS-polyacrylamide gel electrophoresis. The concentration of the thyroglobulin was determined from absorbance at 280 nm using absorption coefficient of 1.0 l/g·cm.

Preparation of thyroglobulin-peroxidase (labeled antigen)

1. Preparation of mercaptosuccinyl-thyroglobulin

Thiol groups were introduced into the purified thyroglobulin by a known method [Ishikawa et al., Journal of Immunoassay, vol. 4, p. 209 (1983)] using S-acetylmercapto-succinic anhydride. The number of the thiol groups introduced was 3.8 per 1 molecule of the thyroglobulin.

2. Preparation of maleimide-peroxidase

Maleimide groups were introduced into horseradish peroxidase by a known method [Hashida et al., Journal of Applied Biochemistry, vol. 6, p. 56 (1984)] using N-succinimidyl-6-maleimidohexanoate. The number of the maleimide groups introduced was 1.3 per 1 molecule of the peroxidase.

3. Preparation of thyroglobulin-peroxidase 0.1M Sodium phosphate buffer (70 µl, pH 6.0) containing mercaptosuccinyl-thyroglobulin (310 µg) and 5 mM EDTA, and 0.1 M sodium phosphate buffer (5 µl, pH 6.0) containing maleimide-peroxidase (93 µg) and 5 mM EDTA were reacted at 4° C. for 20 hours. The reaction mixture was subjected to gel filtration using ultrogel AcA22 column (1.6×45 cm) and 0.1M sodium phosphate buffer, pH 6.5. The number of the peroxidase introduced was 1.7 per 1 molecule of the thyroglobulin.

Preparation of thyroglobulin-bound solid phase (carrier-bound antigen)

Using a solution of the purified thyroglobulin (0.01 g/l), thyroglobulin was bound to the surface of each well of a microplate [33 mm$^2$×11.3 mm, Maxisoap F8 (Nunc, Denmark)] by a known method [Ishikawa et al., Scandinavian Journal of Immunology, vol. 8 (Suppl. 7), p. 43 (1978)] utilizing physical adsorption.

Assay of human anti-thyroglobulin antibody

Test samples (0.05 ml) obtained by diluting sera from patients with Basedow's disease, the anti-thyroglobulin antibody concentration thereof having been identified in advance, to various concentrations with sera of healthy humans, and 0.01M sodium phosphate buffer (0.1 ml, pH 7.0) containing thyroglobulin-peroxidase (100 fmol), 0.55M sodium chloride, 0.1% bovine serum albumin and 0.15% Tween 20 were placed in each well of the thyroglobulin-bound plate (solid phase), and the plate was left standing at room temperature for 2 hours to allow reaction. Each well was washed three times with 0.01M sodium phosphate buffer (0.3 ml, pH 7.0) containing 0.1M sodium chloride and 0.1% Tween 20. Then, 0.01M sodium phosphate buffer (0.15 ml, pH 7.0) containing thyroglobulin-peroxidase (50 fmol), 0.1M sodium chloride, 0.1% bovine serum albumin and 0.1% Tween 20 was added, and the plate was left standing at room temperature for 1 hour to allow reaction. Each well was washed three times with the above-mentioned washing solution and the activity of peroxidase bound to the plate was assayed as in the following.

Assay of peroxidase activity

A substrate solution (150 µl, 0.05M sodium phosphate-citrate buffer, pH 4.8, containing 0.017% hydrogen peroxide and 0.6 mg/ml o-phenylenediamine) was added to each well and the plate was left standing at room temperature for 30 minutes. 2N Sulfuric acid (50 μl) was added to each well to stop the reaction. The activity of peroxidase which formed a complex was determined by measuring absorbance at 492 nm of the reaction mixture in each well. The results are shown in FIG. 1.

A conventional assay method (Comparative Example 1) wherein the target specific antibody is sandwiched by carrier-bound antigen and labeled anti-Ig antibody and a conventional assay method (Comparative Example 2) wherein the target specific antibody is sandwiched in two steps by carrier-bound antigen and labeled antigen are shown in the following as comparative examples for the present invention.

COMPARATIVE EXAMPLE 1

Purification of thyroglobulin, preparation of thyroglobulin-bound solid phase and assay of peroxidase activity were performed according to the method of Example 1.
Assay of human anti-thyroglobulin antibody Test samples (0.05 ml) obtained by diluting sera from patients with Basedow's disease, the concentration of the anti-thyroglobulin antibody thereof having been identified in advance, to various concentrations with sera of healthy humans, and 0.01M sodium phosphate buffer (0.1 ml, pH 7.0) containing 0.55M sodium chloride, 0.1% bovine serum albumin and 0.15% Tween 20 were placed in each well of the thyroglobulin-bound plate (solid phase), and the plate was left standing at room temperature for 2 hours to allow reaction. Each well was washed three times with 0.01M sodium phosphate buffer (0.3 ml, pH 7.0) containing 0.1M sodium chloride and 0.1% Tween 20. 0.01M Sodium phosphate buffer (0.15 ml, pH 7.0) containing peroxidase-labeled affinity purified goat anti-human IgG (7.5 ng, Cappel, Md.), 0.1M sodium chloride, 0.1% bovine serum albumin and 0.1% Tween 20 was added, and the plate was left standing at room temperature for 2 hours to allow reaction. Each well was washed three times with the above-mentioned washing solution and the activity of peroxidase bound to the solid phase was assayed. The results are shown in FIG. 1.

COMPARATIVE EXAMPLE 2

Purification of thyroglobulin, preparation of thyroglobulin-peroxidase, preparation of thyroglobulin-bound solid phase and assay of peroxidase activity were performed according to the method of Example 1.
Assay of human anti-thyroglobulin antibody Test samples (0.05 ml) obtained by diluting the sera from patients with Basedow's disease, the concentration of the anti-thyroglobulin antibody thereof having been identified in advance, to various concentrations with sera of healthy humans, and 0.01M sodium phosphate buffer (0.1 ml, pH 7.0) containing 0.55M sodium chloride, 0.1% bovine serum albumin and 0.15% Tween 20 were placed in each well of the thyroglobulin-bound plate (solid phase), and the plate was left standing at room temperature for 2 hours to allow reaction. Each well was washed three times with 0.01M sodium phosphate buffer, pH 7.0, containing 0.1M sodium chloride and 0.1% Tween 20. 0.01M Sodium phosphate buffer (0.15 ml, pH 7.0) containing thyro-globulin-peroxidase (100 fmol), 0.1M sodium chloride, 0.1% bovine serum albumin and 0.1% Tween 20 was added, and the plate was left standing at room temperature for 2 hours to allow reaction. Each well was washed three times with the above-mentioned washing solution and the activity of peroxidase bound to the solid phase was assayed. The results are shown in FIG. 1.

An example using a different carrier-bound antigen is given as another example of the present invention.

EXAMPLE 2

Purification of thyroglobulin, preparation of thyroglobulin-peroxidase, assay of human anti-thyroglobulin antibody and assay of peroxidase activity were performed according to the method of Example 1.
Preparation of solid phase bound to dinitrophenyl-thyroglobulin-bound rabbit (anti-dinitrophenyl-bovine serum albumin) IgG (carrier-bound antigen)

1. Preparation of solid phase bound with rabbit (anti-dinitrophenyl-bovine serum albumin) IgG Sodium sulfate (0.747 g) was portionwise added to rabbit (anti-dinitrophenyl-bovine serum albumin) antiserum (4.23 g, Seikagaku Kogyo, Tokyo), and the mixture was stirred at room temperature for 30 minutes and centrifuged at 10,000×g for 15 minutes. The precipitate was dissolved in 0.0175M sodium phosphate buffer (4.0 ml, pH 6.3) and dialyzed against the same buffer. The dialysate was subjected to anion exchange chromatography using DE-52 cellulose (Whatman, Kent, UK) column (1.6×8.0 cm) with the linear concentration gradient of sodium chloride. Using this solution, rabbit (anti-dinitrophenyl-bovine serum albumin) IgG was bound to the surface of each well of a microplate [33 mm$^2$×11.3 mm, Maxisoap F8 (Nunc, Denmark)] by a known method [Ishikawa et al., Scandinavian Journal of Immunology, ibid.] utilizing physical adsorption.

2. Preparation of dinitrophenyl-thyroglobulin (1) Synthesis of succinimidyl-2,4-dinitrophenyl-ε-caproic acid 2,4-Dinitrophenyl-ε-caproic acid (Sigma, Missouri) and N-hydroxysuccinimide (Wako Pure Chemical Industries Ltd., Osaka) were condensed by a known method [F. Levi-Schaffer et al., American Journal of Tropical Medicine and Hygiene, vol. 32, p. 343 (1983)] using dichlorocarbodiimide (Wako Pure Chemical Industries Ltd.) to synthesize succinimidyl-2,4-dinitrophenyl-ε-caproic acid. The acid was purified by silica gel (40 g) column in a chloroform/methanol [40/1 (v/v)] system, and the structure was confirmed by NMR (nuclear magnetic resonance) and mass spectrum.

(2) Preparation of dinitrophenyl-thyroglobulin

N,N-Dimethylformamide (60 μl) containing succinimidyl-2,4-dinitrophenyl-ε-caproic acid (66 nmol) prepared in the above (1) was added to 0.1M sodium phosphate buffer (0.6 ml, pH 7.0) containing 0.5 mg of purified thyroglobulin dissolved therein, and the mixture was reacted at 30° C. for 30 minutes. After the reaction, the reaction mixture was subjected to gel filtration using 0.1M sodium phosphate buffer, pH 7.0, and Sephadex G-25 (Pharmacia, Sweden) column (1.0×30 cm). The number of the dinitrophenyl groups introduced was 11 per 1 molecule of the thyroglobulin.

The dinitrophenyl groups were quantitatively determined from the absorbance at 360 nm using an absorption coefficient of 17400/M·cm.

3. Preparation of solid phase bound with dinitrophenyl-thyroglobulin-bound rabbit (anti-dinitrophenyl-bovine serum albumin) IgG 0.01M Sodium phosphate buffer (0.15 ml, pH 7.0) containing dinitrophenyl-thyroglobulin (500 fmol) prepared in the above 2., 0.1M sodium chloride, 0.1% bovine serum albumin and 0.1% sodium azide was added to the plate (solid phase) bound with rabbit (anti-dinitrophenyl-bovine serum albumin) IgG, prepared in the above 1., and the reaction was carried out at 4° C. for 16 hours. After the reaction, the plate was washed with the same buffer, and stored with 0.3 ml of the buffer added thereto.

Assay of human anti-thyroglobulin antibody

In the same manner as in Example 1 except that the thyroglobulin-bound plate (solid phase), i.e. a carrier-bound antigen, was replaced with a plate (solid phase) bound with dinitrophenyl-thyroglobulin-bound rabbit (anti-dinitrophenyl-bovine serum albumin) IgG, the activity of peroxidase bound to the plate was assayed. The results are shown in FIG. 1.

A conventional assay (Comparative Example 3) wherein the target specific antibody is sandwiched by hapten-bound antigen and labeled antigen, and trapped by a carrier bound with an anti-hapten antibody is given as a comparative example for the present invention.

COMPARATIVE EXAMPLE 3

Purification of thyroglobulin, preparation of thyroglobulin-peroxidase and assay of peroxidase activity were performed according to the method of Example 1, and preparation of dinitrophenyl-thyroglobulin and a solid phase bound with rabbit (anti-dinitrophenyl-bovine serum albumin) IgG were performed according to the method of Example 2.

Assay of human anti-thyroglobulin antibody

Test samples (0.05 ml) obtained by diluting the sera from patients with Basedow's disease, the concentration of the anti-thyroglobulin antibody thereof having been identified in advance, to various concentrations with sera of healthy humans, and 0.01M sodium phosphate buffer (0.1 ml, pH 7.0) containing thyroglobulin-peroxidase (100 fmol), dinitrophenyl-thyroglobulin (100 fmol), 0.55M sodium chloride, 0.1% bovine serum albumin and 0.15% Tween 20 were placed in each well of a plate (solid phase) bound with anti-dinitrophenyl-bovine serum albumin IgG, and the plate was left standing at room temperature for 3 hours to allow reaction. Each well was washed three times with 0.01M sodium phosphate buffer (0.3 ml, pH 7.0) containing 0.1M sodium chloride and 0.1% Tween 20, and the activity of the peroxidase bound to the solid phase was assayed. The results are shown in FIG. 1.

As is evident from the results of Examples 1–2 and Comparative Examples 1–3 as shown in FIG. 1, the target specific antibody was assayed with high sensitivity which was about 100 times greater in comparison with Comparative Example 1, and about 10 times greater in comparison with Comparative Example 2, and the problem of prozoning phenomenon which occurred in Comparative Example 3 could be resolved. As shown in Example 2, the use of a carrier-bound antigen different from that in Example 1 also led to the above-mentioned effects.

In the following, the above-mentioned Examples 1 and 2 wherein different labeled antigens were used are described as Examples 3 and 4.

EXAMPLE 3

Purification of thyroglobulin, preparation of thyroglobulin-bound solid phase and assay of human anti-thyroglobulin antibody were performed according to the method of Example 1.

Preparation of thyroglobulin-β-D-galactosidase (labeled antigen)

1. Preparation of maleimide-thyroglobulin 0.55 mM N-Succinimidyl-6-maleimidohexanoate (0.2 ml) dissolved in dimethylformamide was added to purified thyroglobulin (1.08 mg) dissolved in 0.1M sodium phosphate buffer (2.0 ml, pH 7.0), and the mixture was allowed to react at 30° C. for 30 minutes. After the reaction, the reaction mixture was subjected to gel filtration using Sephadex G-25 column (1×30 cm) equilibrated with 0.1M sodium phosphate buffer, pH 6.0, containing 5 mM EDTA, to give maleimide-thyroglobulin. The number of the maleimide groups introduced was 4 per 1 molecule of the thyroglobulin.

2. Preparation of thyroglobulin-β-D-galactosidase

β-D-Galactosidase (0.45 mg) dissolved in 0.1M sodium phosphate buffer (85 μl, pH 6.0) containing 5 mM EDTA was added to maleimide-thyroglobulin (0.55 mg) dissolved in said buffer (50 μl) containing 5 mM EDTA, and the mixture was allowed to react at 4° C. for 2 hours. The reaction mixture was subjected to gel filtration using ultrogel AcA22 column (1.6×70 cm) equilibrated with 0.01M sodium phosphate buffer, pH 7.0, containing 0.1M sodium chloride, 0.1% bovine serum albumin, 0.1 mM $MgCl_2$ and 0.1% $NaN_3$, to give thyroglobulin-β-D-galactosidase. The number of the β-D-galactosidase introduced was 1 per 1 molecule of the thyroglobulin.

Assay of human anti-thyroglobulin antibody

In the same manner as in Example 1 except that the thyroglobulin-peroxidase was replaced with thyroglobulin-β-D-galactosidase, the activity of β-D-galactosidase bound to the plate was assayed.

Assay of β-D-galactosidase activity

The β-D-galactosidase activity was determined using 4-methylumbelliferyl β-D-galactoside as a substrate after the reaction at room temperature for 30 minutes [Imagawa et al., Annals Clinical Biochemistry, vol. 21, p. 310 (1984)]. The fluorescent intensity was corrected based on the fluorescent intensity of 0.1M glycine-NaOH buffer, pH 10.3, containing $10^{-8}$M 4-methylumbelliferone (4 MU) dissolved therein as being 100. The results are shown in FIG. 2.

EXAMPLE 4

Purification of thyroglobulin and assay of human anti-thyroglobulin antibody were performed according to the method of Example 1, preparation of a solid phase bound with dinitrophenyl-thyroglobulin-bound rabbit (anti-dinitrophenyl-bovine serum albumin) IgG were performed according to the method of Example 2, and preparation of thyroglobulin-β-D-galactosidase and assay of β-D-galactosidase activity were performed according to the method of Example 3.

Assay of human anti-thyroglobulin antibody

In the same manner as in Example 3 except that the thyroglobulin-bound solid phase was replaced with a solid phase bound with dinitrophenyl-thyroglobulin-bound rabbit (anti-dinitrophenyl-bovine serum albumin) IgG, the activity of β-D-galactosidase bound to the plate was assayed. The results are shown in FIG. 2.

An example wherein, in the assay of the above-mentioned Comparative Example 2, the same labeled antigen as in the above-mentioned Examples 3 and 4 was used, is shown as a comparative example.

COMPARATIVE EXAMPLE 4

Purification of thyroglobulin and preparation of thyroglobulin-bound solid phase were performed according to the method of Example 1, and preparation of thyroglobulin-β-D-galactosidase and assay of β-D-galactosidase activity were performed according to the method of Example 3.

Assay of human anti-thyroglobulin antibody

In Comparative Example 2, thyroglobulin-peroxidase was replaced with thyroglobulin-β-D-galactosidase. The activity of β-D-galactosidase bound to the plate was assayed in the same manner as in Example 3. The results are shown in FIG. 2.

As is evident from the results of Examples 3–4 and Comparative Example 4 as shown in FIG. 2, it was confirmed that the target specific antibody could be assayed with high sensitivity, even when a labeled antigen different from those used in Examples 1 and 2 was used.

What is claimed is:

1. A method for assaying a specific antibody, comprising the steps of:

(i) forming a complex of a labeled antigen-a specific antibody-a carrier-bound antigen in a first reaction system comprising a mixture of the labeled antigen against the specific antibody to be assayed, the carrier-bound antigen against the specific antibody, and a liquid sample comprising the specific antibody;

(ii) separating the carrier from said first reaction system including incomplete complex of labeled antigen-specific antibody, unreacted specific antibody and unreacted labeled antigen;

(iii) mixing the separated carrier and labeled antigen, thereby forming a second reaction system;

(iv) separating the carrier from the second reaction system including unreacted labeled antigen; and (v) assaying the amount of the label bound to the separated carrier.

2. The method of claim 1, wherein, in (i), the molar ratio of the carrier-bound antigen to the labeled antigen is from 1:1 to 50:1.

3. The method of claim 1, wherein, in (i), the molar ratio of the carrier-bound antigen to the labeled antigen is from 5:1 to 20:1.

4. The method of claim 1, wherein, in (i), the label and the antigen of the labeled antigen are bound via a spacer.

5. The method of claim 1, wherein, in (i), the carrier and the antigen of the carrier-bound antigen are bound via a spacer.

6. The method of claim 4 or claim 5, wherein the spacer is bovine serum albumin.

7. The method of claim 1, wherein, in (i), the label is a peroxidase or β-D-galactosidase.

8. The method of claim 1, wherein the molar ratio of the labeled antigen to be mixed in (i) to the labeled antigen to be mixed in (iii) is in the range of from 1:1 to 10:1.

9. The method of claim 1, wherein, in (iii), the separated carrier is washed after separation of the carrier before mixing the separated carrier with the labeled antigen.

10. The method of claim 1, wherein the specific antibody is an anti-thyroglobulin antibody.

* * * * *